(12) United States Patent
Rebec et al.

(10) Patent No.: US 8,452,365 B2
(45) Date of Patent: ***May 28, 2013

(54) METHODS OF USING RAMAN SPECTRAL INFORMATION IN DETERMINING ANALYTE CONCENTRATIONS

(75) Inventors: Mihailo V. Rebec, Bristol, IN (US); Michael P. Houlne, Centennial, CO (US)

(73) Assignee: Bayer HealthCare LLC, Tarrytown, NY (US)

( * ) Notice: Subject to any disclaimer, the term of this patent is extended or adjusted under 35 U.S.C. 154(b) by 1042 days.

This patent is subject to a terminal disclaimer.

(21) Appl. No.: 11/920,599

(22) PCT Filed: May 24, 2006

(86) PCT No.: PCT/US2006/020015
§ 371 (c)(1),
(2), (4) Date: Feb. 23, 2009

(87) PCT Pub. No.: WO2006/127766
PCT Pub. Date: Nov. 30, 2006

(65) Prior Publication Data
US 2009/0177052 A1     Jul. 9, 2009

Related U.S. Application Data

(60) Provisional application No. 60/684,605, filed on May 25, 2005.

(51) Int. Cl.
*A61B 5/00* (2006.01)
(52) U.S. Cl.
USPC ........................................ 600/335

(58) Field of Classification Search
USPC ............................... 600/310, 335, 322
See application file for complete search history.

(56) References Cited

U.S. PATENT DOCUMENTS

| 4,634,276 A | 1/1987 | Sharpe ..................... 356/305 |
| 4,645,340 A | 2/1987 | Graham et al. ............... 356/301 |

(Continued)

FOREIGN PATENT DOCUMENTS

| EP | 0 129 289 B1 | 9/1990 |
| EP | 0 636 232 B1 | 1/1998 |

(Continued)

OTHER PUBLICATIONS

Berger et al., "Feasibility of Measuring Blood Glucose Concentration by Near-Infrared Raman Spectroscopy," Spectrochimica Acta. Part A: Molecular Spectroscopy, Pergamon Press, Oxford, GB, vol. 53A, No. 2, dated Feb. 1997, pp. 287-292.

(Continued)

*Primary Examiner* — Max Hindenburg
(74) *Attorney, Agent, or Firm* — Nixon Peabody LLP

(57) ABSTRACT

A non-invasive method of determining the concentration of an analyte uses Raman spectral information. A high-intensity, narrow band of light (10) is applied to one side (12*a*) of skin tissue (12). The high-intensity light (10) enters the skin tissue and generates a Raman signal (16). A reflective material (22) is placed in a location nearest the other side (12*b*) of skin tissue (12). The reflective material (22) is located generally opposite of the entry (A) of the applied high-intensity light (10). The high-intensity light (10) and the Raman signal (20) that pass through the skin tissue (12) are reflected back into the skin tissue (12) via the reflective material (22). The Raman signal (16,20) is collected and the analyte concentration is determined using the collected Raman signal (16,20).

13 Claims, 2 Drawing Sheets

U.S. PATENT DOCUMENTS

| | | | | |
|---|---|---|---|---|
| 5,099,123 | A | 3/1992 | Harjunmaa | |
| 5,183,042 | A | 2/1993 | Harjunmaa et al. | |
| 5,370,114 | A | 12/1994 | Wong et al. | |
| 5,372,135 | A | 12/1994 | Mendelson et al. | |
| 5,560,356 | A | 10/1996 | Peyman | 128/633 |
| 5,615,673 | A | 4/1997 | Berger et al. | 128/633 |
| 5,710,630 | A | 1/1998 | Essenpreis et al. | |
| 5,754,289 | A | 5/1998 | Ozaki et al. | 356/301 |
| 5,923,482 | A | 7/1999 | Gilby | 359/846 |
| 6,044,285 | A | 3/2000 | Chaiken et al. | 600/316 |
| 6,070,093 | A | 5/2000 | Oosta et al. | 600/316 |
| 6,137,641 | A | 10/2000 | Gilby | 359/846 |
| 6,167,290 | A | 12/2000 | Yang et al. | 600/322 |
| 6,222,189 | B1 | 4/2001 | Misner et al. | |
| 6,223,063 | B1 | 4/2001 | Chaiken et al. | 600/310 |
| 6,289,230 | B1 | 9/2001 | Chaiken et al. | 600/322 |
| 6,292,686 | B1 | 9/2001 | Chaiken et al. | 600/476 |
| 6,332,092 | B1 | 12/2001 | Deckert et al. | 600/476 |
| 6,352,502 | B1 | 3/2002 | Chaiken et al. | 600/4.73 |
| 6,377,828 | B1 | 4/2002 | Chaiken et al. | 600/316 |
| 6,389,306 | B1 | 5/2002 | Chaiken et al. | 600/474 |
| 6,486,948 | B1 | 11/2002 | Zeng | 356/301 |
| 6,503,478 | B2 | 1/2003 | Chaiken et al. | 424/9.1 |
| 6,560,478 | B1 | 5/2003 | Alfano et al. | 600/473 |
| 6,574,490 | B2 | 6/2003 | Abbink et al. | 600/316 |
| 6,615,061 | B1 | 9/2003 | Khalil et al. | 600/310 |
| 6,636,305 | B2 | 10/2003 | Zhao et al. | 356/300 |
| 6,681,133 | B2 | 1/2004 | Chaiken et al. | 600/473 |
| 6,690,966 | B1 | 2/2004 | Rava et al. | 600/473 |
| 7,226,166 | B2 | 6/2007 | Della Vecchia et al. | 351/221 |
| 7,308,293 | B2 | 12/2007 | Gerlitz | 600/318 |
| 7,603,151 | B2 | 10/2009 | Rebec et al. | |
| 2003/0023170 | A1 | 1/2003 | Gardner et al. | 600/476 |
| 2003/0071993 | A1 | 4/2003 | Zhao et al. | 356/300 |
| 2003/0120137 | A1* | 6/2003 | Pawluczyk | 600/310 |
| 2004/0152992 | A1 | 8/2004 | Zeng | 600/476 |
| 2004/0257529 | A1 | 12/2004 | Thomas | 351/205 |
| 2005/0043597 | A1 | 2/2005 | Xie | 600/315 |
| 2006/0001870 | A1 | 1/2006 | Voigt et al. | 356/301 |
| 2008/0051645 | A1 | 2/2008 | Rebec et al. | 600/316 |
| 2008/0059100 | A1 | 3/2008 | Smous et al. | 702/104 |
| 2010/0022860 | A1 | 1/2010 | Rebec et al. | |

FOREIGN PATENT DOCUMENTS

| | | |
|---|---|---|
| GB | 2 328 279 | 2/1999 |
| WO | WO 03/011764 A3 | 2/2003 |
| WO | WO 03/023339 A1 | 3/2003 |
| WO | WO 03/056311 AI | 7/2003 |
| WO | WO 2004/023125 A2 | 3/2004 |
| WO | WO 2004/064627 A1 | 8/2004 |
| WO | WO 2006/127766 A1 | 11/2006 |

OTHER PUBLICATIONS

Written Opinion corresponding to International Patent Application No. PCT/US2006/020015, European Patent Office, dated Sep. 20, 2006, 8 pages.

International Search Report corresponding to International Patent Application No. PCT/US2006/020015, European Patent Office, dated Sep. 20, 2006, 4 pages.

Z. Huang, H. Zeng, I. Hamzavi, D. McLean, and H. Lui, "Rapid Near-Infrared Raman Spectroscopy System for Real-Time In Vivo Skin Measurements", Optics Letters, 26 (22), 1782-1784 (2001).

"A Noninvasive Glucose Monitor: Preliminary Results in Rabbits" by Mark S. Borchert, M.D., et al., *Diabetes Technology & Therapeutics*, vol. 1, No. 2, 1999, Mary Ann Liebert, Inc. (pp. 145-151).

"Laser-Based Measurement of Glucose in the Ocular Aqueous Humor: An Efficacious Portal for Determination of Serum Glucose Levels" by Paul G. Steffes, Ph.D., *Diabetes Technology & Therapeutics*, vol. 1, No. 2, 1999, Mary Ann Liebert, Inc. (pp. 129-133).

\* cited by examiner

METHODS OF USING RAMAN SPECTRAL INFORMATION IN DETERMINING ANALYTE CONCENTRATIONS

Cross-Reference to Related Applications

This application claims priority to Application No. 60/684,605 filed on May 25, 2005, which is incorporated by reference in its entirety.

FIELD OF THE INVENTION

The present invention generally relates to a method of determining the concentration of an analyte. More specifically, the present invention is directed to a non-invasive method of determining the concentration of an analyte using Raman spectral information.

BACKGROUND OF THE INVENTION

The quantitative determination of analytes in body fluids is of great importance in the diagnoses and maintenance of certain physiological abnormalities. For example, lactate, cholesterol and bilirubin should be monitored in certain individuals. In particular, determining glucose in body fluids is important to diabetic individuals who must frequently check the glucose level in their body fluids to regulate the glucose intake in their diets. The results of such tests can be used to determine what, if any, insulin or other medication needs to be administered.

Determining the analyte concentration of, for example, glucose is typically performed by invasive methods. It would be desirable to determine such analyte concentrations by using a non-invasive method.

Non-invasive methods may incorporate the use of different types of signals to determine the analyte concentration. One type of signal is a Raman spectral signal. The use of Raman spectral information, however, has had limited application in determining non-invasive analyte concentrations because the signals tend to be very weak. There a number of factors that contribute to the very weak Raman signal collected from the skin. One factor is the limited amount of high intensity energy that one can safely deliver into tissue without causing photodamage to the tissue. A second factor is the limited Raman scattering efficiency inherent to most molecules of analytical and physiological interest. A third factor is the scattering and absorbance characteristics of the tissue that limit the amount of energy that can be effectively delivered into the tissue and the amount of Raman spectral information that can be collected from the tissue.

It would be desirable to develop a non-invasive method using Raman spectral information in determining the analyte concentration.

SUMMARY OF THE INVENTION

According to one non-invasive method, the concentration of an analyte is determined using Raman spectral information. A high-intensity, narrow band of light is applied to one side of skin tissue. The high-intensity light enters the skin tissue and generates a Raman signal. A reflective material is placed in a location nearest the other side of skin tissue. The reflective material is located generally opposite of the entry of the applied high-intensity light. The high-intensity light and the Raman signal that pass through the skin tissue are reflected back into the skin tissue via the reflective material. The Raman signal is collected and the analyte concentration is determined using the collected Raman signal.

According to another non-invasive method, the concentration of an analyte is determined using Raman spectral information. An area of the skin is pinched. Reflective material is placed near or around the pinched skin tissue. The reflective material forms at least one opening therethrough. A high-intensity, narrow band of light is applied to one side of skin tissue through the at least one opening. The high-intensity light enters the skin tissue and generates a Raman signal. The high-intensity light and Raman signal that pass through the pinched skin tissue are reflected back into the pinched skin tissue via the reflective material. The Raman signal is collected and the analyte concentration is determined using the collected Raman signals.

According to yet another non-invasive method, the concentration of an analyte is determined using Raman spectral information. A plurality of high-intensity, narrow band of light sources is placed around the skin tissue. The high-intensity light enters the skin tissue and generates a Raman signal. A plurality of detectors is placed around the skin tissue. The Raman signal is collected via the plurality of detectors. The analyte concentration is determined using the collected Raman signal.

DETAILED DESCRIPTION OF THE ILLUSTRATED EMBODIMENTS

The invention is directed to non-invasive methods for determining the concentration of an analyte using Raman spectral information. The invention is adapted to increase optical throughput in these methods using Raman spectral information. Analytes that may be measured using the present invention include glucose, lipid profiles (e.g., cholesterol, triglycerides, LDL and HDL), microalbumin, hemoglobin $A_{1C}$, fructose, lactate, or bilirubin. The present invention is not limited, however, to these specific analytes and it is contemplated that other analyte concentrations may be determined. The analytes may be in, for example, a whole blood sample, a blood serum sample, a blood plasma sample, and other body fluids like ISF (interstitial fluid) and urine.

According to one method, the concentration of an analyte is determined using Raman spectral information. The method comprises applying a high-intensity, narrow band of light to one side of skin tissue. The high-intensity, narrow band of light enters the skin tissue and generates a Raman signal. A reflective material is placed in a location nearest the other side of the skin tissue. The reflective material is located generally opposite of the entry of the applied high-intensity light. The high-intensity light and the Raman signal that pass through the skin tissue are reflected back into the skin tissue via the reflective material. The Raman signal is collected and the analyte concentration is determined using the collected Raman signal.

Figure 1:
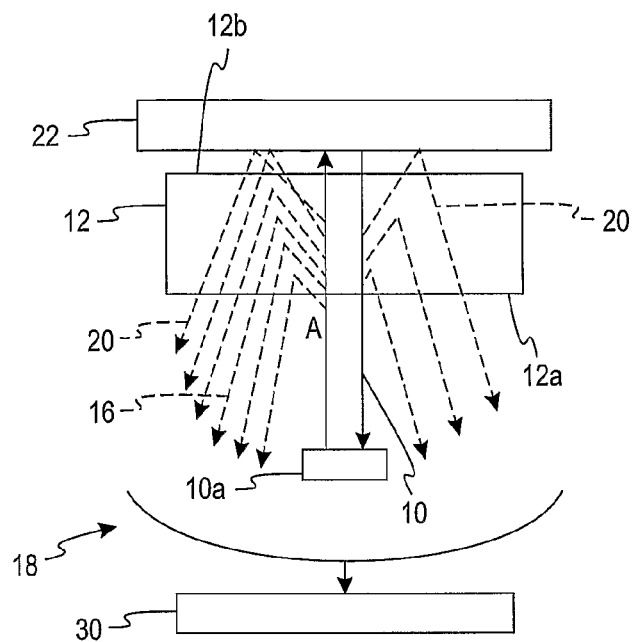
FIG. 1 is an illustration used in determining the concentration of an analyte according to one embodiment.

Referring to FIG. 1, an illustration is used showing the location of the reflective material and the high-intensity, narrow band of light according to one method. High-intensity light 10 is applied to skin tissue 12 such as pinched skin tissue. The high intensity light 10 is shown in FIG. 1 as coming from a high-intensity light source 10a. The high-intensity light source may be a variety of light sources. For example, the high-intensity light source may come from a monochromatic light source that is delivered in a narrow band. One example of a monochromatic light source is a laser-diode source. It is contemplated that other light sources may be used such as a light-emitting diode and zeon-arc lamps. The light sources may be filtered to provide a more clearly defined (i.e., narrow) band of light. It is also contemplated that the high-intensity light may be a dye laser, gas laser, ion laser or a pumped solid-state laser.

One specific example is an 830 nm laser-diode source. One example of a commercially available 830 nm laser-diode source is Invictus™ NIR 830 nm diode laser, which is marketed by Kaiser Optical Systems, Inc of Ann Arbor, Mich. Another example is the PI-ECL-830-500 diode laser, which is marketed by Process Instruments of Salt Lake City, Utah. In one embodiment, the laser light is delivered to the skin tissue in about a 1 mm beam diameter. It is contemplated that other laser-diode sources may be employed.

The Raman spectral information may be collected in the wavelength range from about 300 nm to about 5000 nm. However, several wavelength-dependent characteristics unique to tissue optics and to the Raman effect can significantly impact the ability to successfully employ the Raman technique for the noninvasive determination of analytes in tissue. For example, at lower wavelengths the inherent Raman signal from analytes in tissue is relatively strong, but tissue autofluorescence is also relatively strong, which may complicate detecting the Raman signal in the tissue. Conversely, at higher wavelengths, tissue autofluorescence and the inherent Raman signal decrease. The choice of the light source would be made based on a balance of the Raman signal power and the autofluorescence interference at the wavelengths of interest for the analyte of interest. Therefore, for glucose analysis, it is desirable to employ a high-intensity, narrow band light source centered at or near 830 nm and collect the Raman spectral information in the wavelength range of from above 830 nm to about 1030 nm where the strength of the Raman signal is optimized verses the tissue autofluorescence.

The glucose-related Raman spectral information may be collected from Raman scattered light shifted from 100 $cm^{-1}$ to 1600 $cm^{-1}$ away from the light source since the strongest glucose peaks occur at Raman shifts of about 1340 $cm^{-1}$ and about 1125 $cm^{-1}$. It is contemplated that the Raman spectral information may be collected in different ranges, especially if the analyte concentration to be determined is not glucose.

The high-intensity light 10 enters on a side 12a of the skin tissue 12. The thickness of the skin tissue that may be used in determining the analyte concentration may vary. The skin tissue is generally from about 1 to about 5 mm in thickness. More specifically, the skin is generally from about 1 to about 3 mm in thickness. The skin tissue may be pinched when the high-intensity light enters the skin tissue.

As shown in FIG. 1, the high-intensity light 10 enters the skin tissue 12 at point A. After the high-intensity light 10 enters the skin tissue 12, a Raman signal is generated and scatters in all directions. A portion 16 of the Raman signal is redirected back towards collection optics 18. Some of the Raman signal exits the skin tissue 12, however, and is reflected back using a reflective material 22.

The reflective material 22 is placed in a location nearest the other side 12b of the skin tissue 12. The reflective material is located generally opposite of the entry of the applied high-intensity light. As shown in FIG. 1, the reflective material 22 is located opposite of the entry of the high-intensity light 10 at point A in FIG. 1. It is contemplated that the reflective material may be a single reflector as shown in FIG. 1 or a plurality of reflectors.

The reflective material 22 assists in creating and reflecting back a larger quantity of Raman signal. The reflective material 22 reflects back the source light that passes through the skin tissue 12. After this source light is reflected back into the skin tissue 12 via the reflective material 22, it generates an additional Raman signal. Thus, the optical pathlength is increased by passing the source light through the skin tissue twice. By increasing the optical pathlength, the resulting analytical signal is also increased. Additionally, the reflective material 22 reflects back a Raman signal towards the collection optics 18 that would otherwise have been lost exiting the other side 12b of the skin tissue 12, which is opposite of the collection optics 18. Thus, an increased fraction of the Raman signal will be redirected to the collection optics 18. A portion 20 of the Raman signal includes (a) the additional generated Raman signal from the source light that passes through the skin tissue and is reflected back, and (b) and Raman signal reflected back from the reflective material 22.

The reflective material may be formed from a variety of materials. For example, the reflective material may be a gold-plated metal. According to another embodiment, the reflective material is aluminum. To provide a more efficient reflective material, the aluminum, for example, is a shiny aluminum. It is contemplated that other reflective materials may be used in the present invention.

The collection optics 18 collects the returned Raman signal 16, 20. The collected Raman signal is then passed to a detector 30. The detector 30 assists in determining the analyte concentration (e.g., glucose) from the collected Raman signal. One example of a detector that may be used is a silicon detector. Other examples of detectors include an extended InGaAs detector, a germanium detector, or a lead sulfide (PbS) detector. It is contemplated that other detectors may be employed to assist in determining the analyte concentration (e.g., glucose) from the collected Raman signal.

Figure 2:
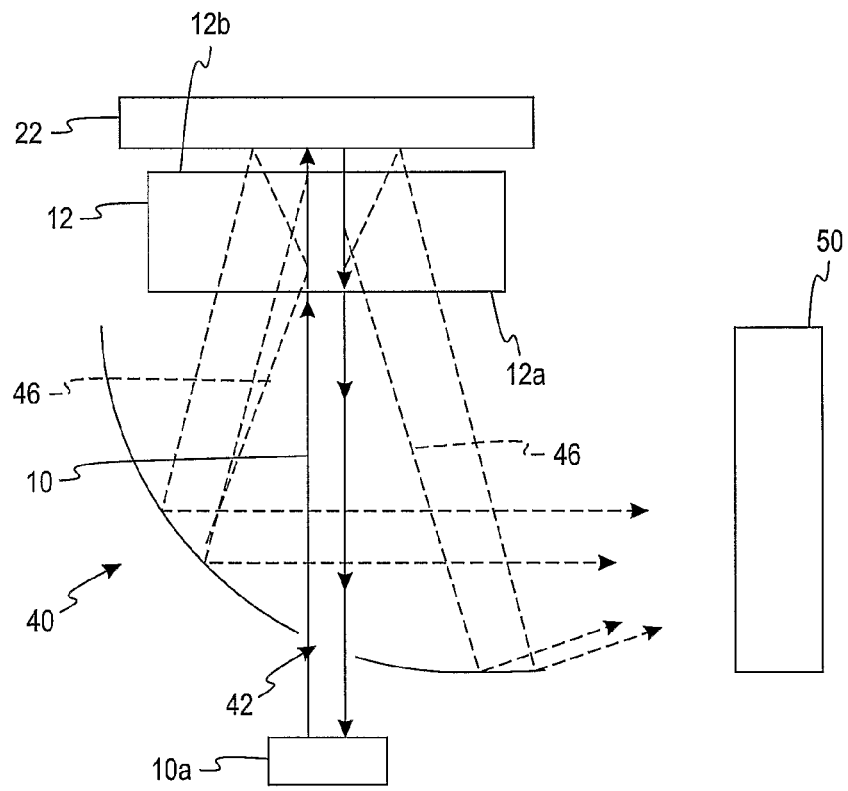
FIG. 2 is an illustration used in determining the concentration of an analyte according to another embodiment.

The collection optics may vary from that depicted in FIG. 1. FIG. 2 depicts an illustration similar to FIG. 1 that includes a parabolic mirror 40 in which the high-intensity light 10 passes through an opening 42 formed therein. The high-intensity light 10 enters the tissue and generates a Raman signal, which is scattered in all directions. The scattered Raman signal 46 is directed back to the parabolic mirror 40. The Raman signal is further reflected by the parabolic mirror to a detector 50 where the analyte concentration is determined from the collected Raman signal.

According to another embodiment, the collection optics may be other mirrors with curvatures that deliver focused laser light back into the tissue. Alternatively, the collection optics may be other mirrors with curvatures that are shaped to deliver parallel light back into the tissue depending on the Raman signal collection optics.

According to another method, a non-invasive method of determining the concentration of an analyte using Raman spectral information includes pinching an area of the skin tissue. A reflective material is placed near or around the pinched skin tissue. The reflective material forms at least one opening therethrough. A high-intensity, narrow band of light is applied to the pinched skin tissue through the at least one opening. The high-intensity light enters the pinched skin tissue and generates a Raman signal. The high-intensity light and Raman signal that pass through the pinched skin tissue are reflected back into the pinched skin tissue via the reflective material. The Raman signal is collected and the analyte concentration is determined using the collected Raman signal.

Figure 3A:
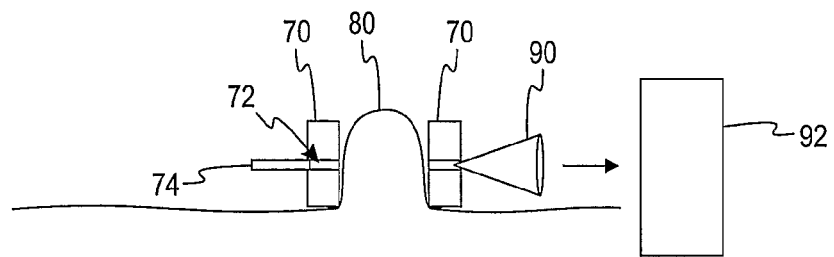
FIG. 3a is an illustration used in determining the concentration of an analyte according to yet another embodiment.

As shown in FIG. 3a, a reflective material 70 is placed near or around a pinched skin tissue 80. The width of the pinched skin tissue is generally from about 1 to about 2 mm. The reflective material 70 forms at least one opening 72 in which the high-intensity light 74 is applied through the at least one opening 72. The high-intensity light 74 enters the pinched skin tissue 80 and generates a Raman signal. The high-intensity light and Raman signal that pass through the pinched skin tissue are reflected back into the pinched skin tissue via the reflective material 70. The Raman signal is collected and the analyte concentration is determined using the collected Raman signal.

Figure 3B:
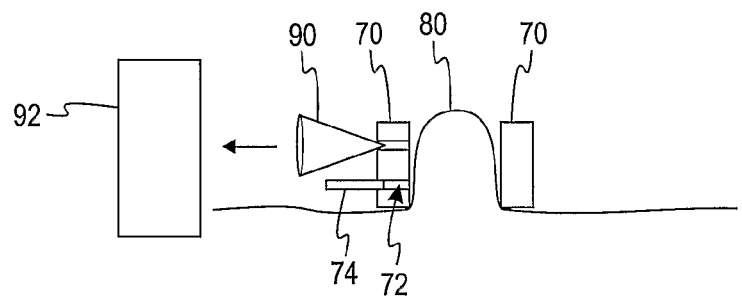
FIG. 3b is an illustration used in determining the concentration of an analyte according to yet another embodiment.

The Raman signal may be collected via high NA (numerical aperture) optics or fiber(s) 90. The high NA (numerical aperture) optics or fiber(s) 90 transmit the collected Raman signals to a spectrometer 92. It is contemplated that the collected signals may be transmitted to a single detector with a filter, a CCD (cathode-coupled detector), a diode array, or other devices that detect a specific signal. It is contemplated that the Raman signal may be collected on the same side as the high-intensity light entering the pinched skin tissue such as shown, for example, in FIG. 3b.

According to another method, a non-invasive method of determining the concentration of an analyte using Raman spectral information includes placing a plurality of high-intensity, narrow band of light sources around the skin tissue. The high-intensity light enters the skin tissue and generates a Raman signal. A plurality of detectors is placed around the skin tissue. The Raman signal is collected via the plurality of detectors. The analyte concentration is determined using the collected Raman signal.

Figure 4:
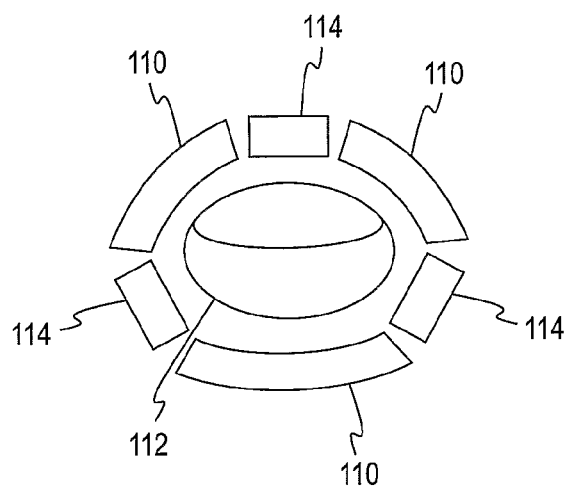
FIG. 4 is ant illustration used in a method of determining the concentration of an analyte.

Referring to FIG. 4, a plurality of high-intensity, narrow band of light sources 110 is placed around skin tissue 112. The high-intensity light enters the skin and generates a Raman signal. A plurality of detectors 114 is placed around the skin tissue 112. The Raman signal is collected via the plurality of detectors 114. The analyte concentration is determined using the collected Raman signal. It is contemplated that the number of and the location of the high-intensity light sources and the detectors may vary from that depicted in FIG. 4.

Alternative Process A

A non-invasive method of determining the concentration of an analyte using Raman spectral information, the method comprising the acts of:

applying a high-intensity, narrow band of light to one side of skin tissue, the high-intensity light entering the skin tissue and generating a Raman signal;

placing a reflective material in a location nearest the other side of skin tissue, the reflective material being located generally opposite of the entry of the applied high-intensity light;

reflecting the high-intensity light and the Raman signal that pass through the skin tissue back into the skin tissue via the reflective material;

collecting the Raman signal; and determining the analyte concentration using the collected Raman signal.

Alternative Process B

The method of Alternative Process A wherein the high-intensity light is applied from a monochromatic light source.

Alternative Process C

The method of Alternative Process B wherein the high-intensity light is applied from a laser-diode source.

Alternative Process D

The method of Alternative Process A wherein the high-intensity light is applied from a light-emitting diode or a zeon-arc lamp.

Alternative Process E

The method of Alternative Process A wherein the high-intensity light is applied from a dye laser, a gas-laser source, an ion-laser source, or a pumped solid-state laser source.

Alternative Process F

The method of Alternative Process A wherein the skin tissue is from about 1 to about 5 mm in thickness.

Alternative Process G

The method of Alternative Process A wherein the reflective material located opposite of the entry of the applied high-intensity light.

Alternative Process H

The method of Alternative Process A wherein the reflective material comprises aluminum.

Alternative Process I

The method of Alternative Process A wherein the reflective material comprises a gold-plated surface.

Alternative Process J

The method of Alternative Process A wherein the reflective material is a plurality of reflectors.

Alternative Process K

The method of Alternative Process A further including a detector that assists in determining the analyte concentration, the detector being a silicon detector.

Alternative Process L

The method of Alternative Process A further including a detector that assists in determining the analyte concentration, the detector being a germanium detector.

Alternative Process M

The method of Alternative Process A further including a detector that assists in determining the analyte concentration, the detector being an InGaAs detector.

Alternative Process N

The method of Alternative Process A further including a detector that assists in determining the analyte concentration, the detector being a lead sulfide detector.

Alternative Process O The method of Alternative Process A wherein the Raman signal is collected using at least one parabolic mirror.

Alternative Process P

The method of Alternative Process A wherein the Raman signal is collected at a wavelength range of from about 300 to about 5000 nm.

Alternative Process Q

The method of Alternative Process P wherein the Raman signal is collected a wavelength range of from about 830 to about 1030 nm.

Alternative Process R

A non-invasive method of determining the concentration of an analyte using Raman spectral information, the method comprising the acts of:

pinching an area of the skin tissue;

placing a reflective material near or around the pinched skin tissue, the reflective material forming at least one opening therethrough;

applying a high-intensity, narrow band of light to the skin tissue through the at least one opening, the high-intensity light entering the skin tissue and generating a Raman signal;

reflecting the high-intensity light and Raman signal that pass through the pinched skin tissue back into the pinched skin tissue via the reflective material;

collecting the Raman signal; and determining the analyte concentration using the collected Raman signal.

Alternative Process S

The method of Alternative Process R wherein the reflective material forms a plurality of openings therethrough and the high-intensity light is applied through the plurality of openings.

Alternative Process T

The method of Alternative Process R wherein the Raman signal is collected via high NA (numerical aperture) optics or fiber(s).

Alternative Process U

The method of Alternative Process R wherein the high-intensity light is applied from a monochromatic light source.

Alternative Process V

The method of Alternative Process U wherein the high-intensity light is applied from a laser diode source.

Alternative Process W

The method of Alternative Process R wherein the reflective material comprises aluminum.

Alternative Process X

The method of Alternative Process R wherein the reflective material comprises a gold-plated surface.

Alternative Process Y

The method of Alternative Process R further including a detector that assists in determining the analyte concentration, the detector being is a silicon detector.

Alternative Process Z

The method of Alternative Process R further including a detector that assists in determining the analyte concentration, the detector being a germanium detector.

Alternative Process AA

The method of Alternative Process R further including a detector that assists in determining the analyte concentration, the detector being an InGaAs detector.

Alternative Process BB

The method of Alternative Process R further including a detector that assists in determining the analyte concentration, the detector being a lead sulfide detector.

Alternative Process CC

The method of Alternative Process R wherein the Raman signal is collected a wavelength range of from about 300 to about 5000 nm.

Alternative Process DD

The method of Alternative Process CC wherein the Raman signal is collected a wavelength range of from about 830 to about 1030 nm.

Alternative Process EE

A non-invasive method of determining the concentration of an analyte using Raman spectral information, the method comprising the acts of:

placing a plurality of high-intensity, narrow band of light sources around the skin tissue, the high-intensity light entering the skin tissue and generating a Raman signal;

placing a plurality of detectors around the skin tissue;

collecting the Raman signal via the plurality of detectors; and determining the analyte concentration using the collected Raman signal.

Alternative Process FF

The method of Alternative Process EE wherein the high-intensity light is applied from a monochromatic light source.

Alternative Process GG

The method of Alternative Process FF wherein the high-intensity light is applied from a laser-diode source.

Alternative Process HH

The method of Alternative Process EE wherein the plurality of detectors is a silicon detector.

Alternative Process II

The method of Alternative Process EE wherein the plurality of detectors is a germanium detector.

Alternative Process JJ

The method of Alternative Process EE wherein the plurality of detectors is an InGaAs detector.

Alternative Process KK

The method of Alternative Process EE wherein the plurality of detectors is a lead sulfide detector.

Alternative Process LL

The method of Alternative Process EE wherein the Raman signal is collected a wavelength range of from about 300 to about 5000 nm n.

Alternative Process MM

The method of Alternative Process LL wherein the Raman signal is collected a wavelength range of from about 830 to about 1030 nm.

While the invention is susceptible to various modifications and alternative forms, specific methods are shown by way of example in the drawings and are described in detail herein. It should be understood, however, that the invention is not intended to be limited to the particular forms disclosed. Rather, the invention is to cover all modifications, equivalents, and alternatives falling within the spirit and scope of the invention as defined by the appended claims.

The invention claimed is:

1. A non-invasive method of determining the concentration of an analyte using Raman spectral information, the method comprising the acts of:

pinching an area of skin tissue;

placing a reflective material near or around the pinched skin tissue, the reflective material forming at least one opening therethrough;

applying a high-intensity, narrow band of light to the skin tissue through the at least one opening, the high-intensity light entering the pinched skin tissue and generating a Raman signal;

reflecting the high-intensity light and Raman signal that pass through the pinched skin tissue back into the pinched skin tissue via the reflective material;

collecting the Raman signal; and determining the analyte concentration using the collected Raman signal, wherein the Raman signal is collected at a wavelength range of from about 300 to about 5000 nm.

2. The method of claim 1, wherein the reflective material forms a plurality of openings therethrough and the high-intensity light is applied through the plurality of openings.

3. The method of claim 1, wherein the Raman signal is collected via high NA (numerical aperture) optics or fiber(s).

4. The method of claim 1, wherein the reflective material comprises aluminum.

5. The method of claim 1, wherein the Raman signal is collected at a wavelength range of from about 830 to about 1030 nm.

6. The method of claim 1, wherein the Raman signal is collected via high NA (numerical aperture) optics or fiber(s).

7. The method of claim 1, wherein the high-intensity light is applied from a monochromatic light source.

8. The method of claim 7, wherein the high-intensity light is applied from a laser diode source.

9. The method of claim 1, wherein the reflective material comprises a gold-plated surface.

10. The method of claim 1, further including a detector that assists in determining the analyte concentration, the detector being a silicon detector.

11. The method of claim 1, further including a detector that assists in determining the analyte concentration, the detector being a germanium detector.

12. The method of claim 1, further including a detector that assists in determining the analyte concentration, the detector being an InGaAs detector.

13. The method of claim 1, further including a detector that assists in determining the analyte concentration, the detector being a lead sulfide detector.

* * * * *